(12) United States Patent
Basamania et al.

(10) Patent No.: US 9,833,327 B2
(45) Date of Patent: Dec. 5, 2017

(54) GLENOID COMPONENT FOR USE IN SHOULDER ARTHROPLASTY

(75) Inventors: Carl Basamania, Seattle, WA (US); Kyle E. Lappin, Fort Wayne, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 1247 days.

(21) Appl. No.: 12/408,391

(22) Filed: Mar. 20, 2009

(65) Prior Publication Data

US 2010/0241235 A1   Sep. 23, 2010

(51) Int. Cl.
*A61F 2/40* (2006.01)
*A61F 2/46* (2006.01)
*A61F 2/30* (2006.01)

(52) U.S. Cl.
CPC .......... *A61F 2/4081* (2013.01); *A61F 2/4612* (2013.01); *A61F 2002/30565* (2013.01); *A61F 2002/30733* (2013.01); *A61F 2002/30772* (2013.01); *A61F 2002/30878* (2013.01); *A61F 2002/30881* (2013.01); *A61F 2002/30894* (2013.01); *A61F 2002/30901* (2013.01); *A61F 2002/4622* (2013.01)

(58) Field of Classification Search
CPC .......... A61F 2/40; A61F 2/4014; A61F 2/4081
USPC ........................................... 623/19.11–19.14
See application file for complete search history.

(56) References Cited

U.S. PATENT DOCUMENTS

| | | | |
|---|---|---|---|
| 3,140,712 A | 7/1964 | Hunter | |
| 3,528,109 A | 9/1970 | Scales | |
| 3,694,820 A | 10/1972 | Scales et al. | |
| 3,781,918 A | 1/1974 | Mathys | |
| 3,978,528 A * | 9/1976 | Crep | 623/19.12 |
| 4,045,825 A | 9/1977 | Stroot | |
| 4,045,826 A | 9/1977 | Stroot | |
| 4,206,517 A | 6/1980 | Pappas et al. | |
| 4,964,865 A * | 10/1990 | Burkhead et al. | 623/19.11 |
| 4,986,833 A | 1/1991 | Worland | |
| 5,593,448 A * | 1/1997 | Dong | 623/19.11 |

(Continued)

FOREIGN PATENT DOCUMENTS

| | | |
|---|---|---|
| EP | 1776935 | 4/2007 |
| WO | 8502535 A1 | 6/1985 |

OTHER PUBLICATIONS

European Search Report in related European Patent Application (i.e., EP 10 15 4941) dated Jun. 21, 2010 (4 pages).

(Continued)

*Primary Examiner* — Christopher D Prone
(74) *Attorney, Agent, or Firm* — Maginot, Moore & Beck, LLP

(57) ABSTRACT

An method includes creating a first bore and a second bore in a glenoid region of a scapula offset from each other by a first distance. A glenoid component is provided that includes a base component having a bearing surface and a first peg and a second peg each extending from a scapula-facing side of the base component and being positioned in non-parallel orientation with respect to each other. At least one of the first peg and the second peg is flexed so that a first end portion of the first peg and a second end portion of the second peg are offset by a second distance which corresponds to the first distance. The first end portion of the first peg and the second end portion of the second peg are then advanced into the first bore and the second bore, respectively.

11 Claims, 12 Drawing Sheets

(56) References Cited

U.S. PATENT DOCUMENTS

| | | | |
|---|---|---|---|
| 5,702,447 A | 12/1997 | Walch et al. | |
| 5,769,856 A | 6/1998 | Dong et al. | |
| 6,228,119 B1 | 5/2001 | Ondrla et al. | |
| 6,364,910 B1 * | 4/2002 | Shultz et al. | 623/19.13 |
| 6,406,495 B1 | 6/2002 | Schoch | |
| 6,514,287 B2 | 2/2003 | Ondrla et al. | |
| 6,699,289 B2 | 3/2004 | Iannotti et al. | |
| 6,911,047 B2 | 6/2005 | Rockwood, Jr. et al. | |
| 7,169,184 B2 | 1/2007 | Dalla Pria | |
| 2003/0055507 A1 * | 3/2003 | McDevitt et al. | 623/19.11 |
| 2006/0200248 A1 | 9/2006 | Beguin et al. | |
| 2007/0016304 A1 | 1/2007 | Chudik | |
| 2007/0142917 A1 | 6/2007 | Roche et al. | |
| 2007/0219638 A1 * | 9/2007 | Jones et al. | 623/19.11 |
| 2007/0244563 A1 * | 10/2007 | Roche et al. | 623/19.12 |
| 2008/0065226 A1 * | 3/2008 | Long et al. | 623/19.14 |

OTHER PUBLICATIONS

European Search Report in corresponding European Patent Application (i.e., EP 12189333.3), dated Jan. 22, 2013 (7 pages).

* cited by examiner

GLENOID COMPONENT FOR USE IN SHOULDER ARTHROPLASTY

BACKGROUND

The present disclosure relates generally to a glenoid component for a use in a shoulder arthroplasty, and an associated method of implanting the glenoid component in a scapula of a patient.

It has become common to perform a shoulder arthroplasty to repair a patient's shoulder joint which has become dysfunctional due to disease or trauma. During such a procedure, the natural glenoid surface of the scapula is resurfaced or otherwise replaced with a prosthetic glenoid component which provides a bearing surface for a head of the humerus or a head portion of a humeral prosthesis (hereinafter "humeral head").

Various glenoid components have heretofore been designed to include a base component that defines a bearing surface on a humeral-facing side and a number of pegs that extend from a scapula-facing side of the base component. These pegs may include relatively long anchor pegs having a plurality of radially extending fins and/or relatively short stabilizing or anti-rotation pegs which may or may not have a series of grooves defined therein. One example of an existing glenoid component possessing the above-described configuration is disclosed in U.S. Pat. No. 6,911,047, the disclosure which is herein incorporated by reference in its entirety.

The pegs of this type of existing glenoid component extend from the scapula-facing side of the base component so that the axes defined by the pegs are parallel with respect to each other. One drawback of glenoid components with parallel oriented pegs is the inability in some instances to reach healthy bone stock remaining in a patient's scapula. In particular, there are many clinical situations in which a patient's scapula possesses deficient bone stock at the locations which align with the relatively long, parallel anchor pegs. Thus, upon implantation of the glenoid component, the anchor pegs reside in deficient bone stock thereby causing an unstable attachment of the glenoid component to the patient's scapula. Interestingly, in many of these clinical situations, healthy bone stock is observed in other locations of the glenoid region of the scapula.

In order to address this problem, some existing glenoid components possess pegs extending from the scapula-facing side of the base component which are divergent with respect to each other. Being configured divergent, the pegs are targeted to be embedded in healthier scapula bone stock for more effective anchoring of the pegs. One example of this type of glenoid component is disclosed in U.S. Pat. No. 5,593,448 (hereinafter "the '448 patent").

However, providing the pegs of the glenoid component with a non-parallel orientation (e.g. divergent or convergent) causes some challenges for implantation of the device. Significantly, during implantation, the pegs of the glenoid component do not physically align with the bores drilled in the scapula for receiving the pegs. In contrast, pegs having a parallel orientation with respect to each other align with drilled bores thereby facilitating implantation of the glenoid component. In order to address the implantation challenge of non-parallel peg type glenoid components, the '448 patent teaches that its base component is configured to flex or deform so as to cause its pegs to become temporarily more aligned with the holes defined in the scapula so that insertion of the pegs therein is enabled.

There are drawbacks associated with providing a glenoid component having a readily flexible or deformable base component. Indeed, the base component of a glenoid component, when implanted, receives a significant amount of force during normal use. In particular, the humeral head articulates against the base component of the glenoid component during normal human use. If the base component flexes or deforms when the humeral head is urged against it, unnatural forces may be applied to the soft tissue and muscles that interconnect the humerus to the scapula. These unnatural forces may cause damage to such soft tissue and muscles. In addition, pain or discomfort to a person in which the glenoid component is implanted may result due to the unnatural forces.

Additionally, creating a base component of a glenoid component from materials that are more flexible or deformable may result in a base component which is less durable in relation to non-flexible or non-deformable base components (i.e. conventional base components). Thus, during normal use of the shoulder joint, articulation of the humeral head against the flexible or deformable base component may cause relatively rapid deterioration of the base component thereby resulting in early failure of the glenoid component. Moreover, wear debris may be more readily generated in such a device.

What is needed therefore is an improved glenoid component that possesses non-parallel oriented pegs (e.g. diverging or converging pegs). What is also needed is an improved method of implanting such a glenoid component in the scapula of a patient. What is further needed is a glenoid component with non-parallel oriented pegs that has a base component which possesses the degree of structural integrity equivalent with base components of conventional glenoid components. What is additionally needed is a glenoid component having non parallel oriented pegs that has a base component that does not flex or deform significantly during articulation of a humeral head thereagainst. What is also need is a glenoid component having non parallel oriented pegs that does not generate significant wear debris during articulation of a humeral head thereagainst. What is further needed is a glenoid component having non parallel oriented pegs that does not cause unnatural forces to be applied to the soft tissue and muscles that interconnect the humerus to the scapula during articulation of the humeral head against the base component of the glenoid component. What is further needed is a glenoid component having non parallel oriented pegs that does not cause damage to such soft tissue and muscles that interconnect the humerus to the scapula during articulation of the humeral head against the base component of the glenoid component. What is also needed is a glenoid component having non parallel oriented pegs that does not cause pain or discomfort to a patient in which the glenoid component is implanted during articulation of the humeral head against the base component of the glenoid component. Additional features and advantages of the present disclosure will become apparent to those skilled in the art upon consideration of the following detailed description of the preferred embodiments.

SUMMARY

In accordance with one embodiment of the present disclosure, there is provided an implantation method. The method includes creating a first bore and a second bore in a glenoid region of a scapula so that a first opening defined by the first bore and a second opening defined by the second bore are offset by a first distance. The method further includes providing a glenoid component that includes (i) a base component having a bearing surface defined on a humeral-facing side thereof, (ii) a first peg extending from a scapula-facing side of the base component, and (iii) a second peg extending from the scapula-facing side of the base component, the first peg and the second peg being positioned in non-parallel orientation with respect to each other. The method also includes flexing at least one of the first peg and the second peg so that a first end portion of the first peg and a second end portion of the second peg are offset by a second distance which corresponds to the first distance. In addition, the method includes advancing the first end portion of the first peg and the second end portion of the second peg into the first bore and the second bore, respectively, while the first end portion of the first peg and the second end portion of the second peg are offset by the second distance.

Pursuant to another embodiment of the present disclosure, there is provided a glenoid assembly that includes a base component having a humeral-facing side and a scapula-facing side, the base component defining a bearing surface defined on the humeral-facing side. The glenoid assembly further includes a first peg extending from the scapula-facing side of the base component. In addition, the glenoid assembly includes a second peg extending from the scapula-facing side of the base component. The first peg and the second peg are positioned in non-parallel orientation with respect to each other. The first shaft defines a first shaft diameter equal to FD and a first shaft length equal to FL. The second shaft defines a second shaft diameter equal to SD and a second shaft length equal to SL, wherein $0.14<FD/FL<0.24$, and wherein $0.14<SD/SL<0.24$.

DESCRIPTION OF THE PREFERRED EMBODIMENTS

Figure 1:
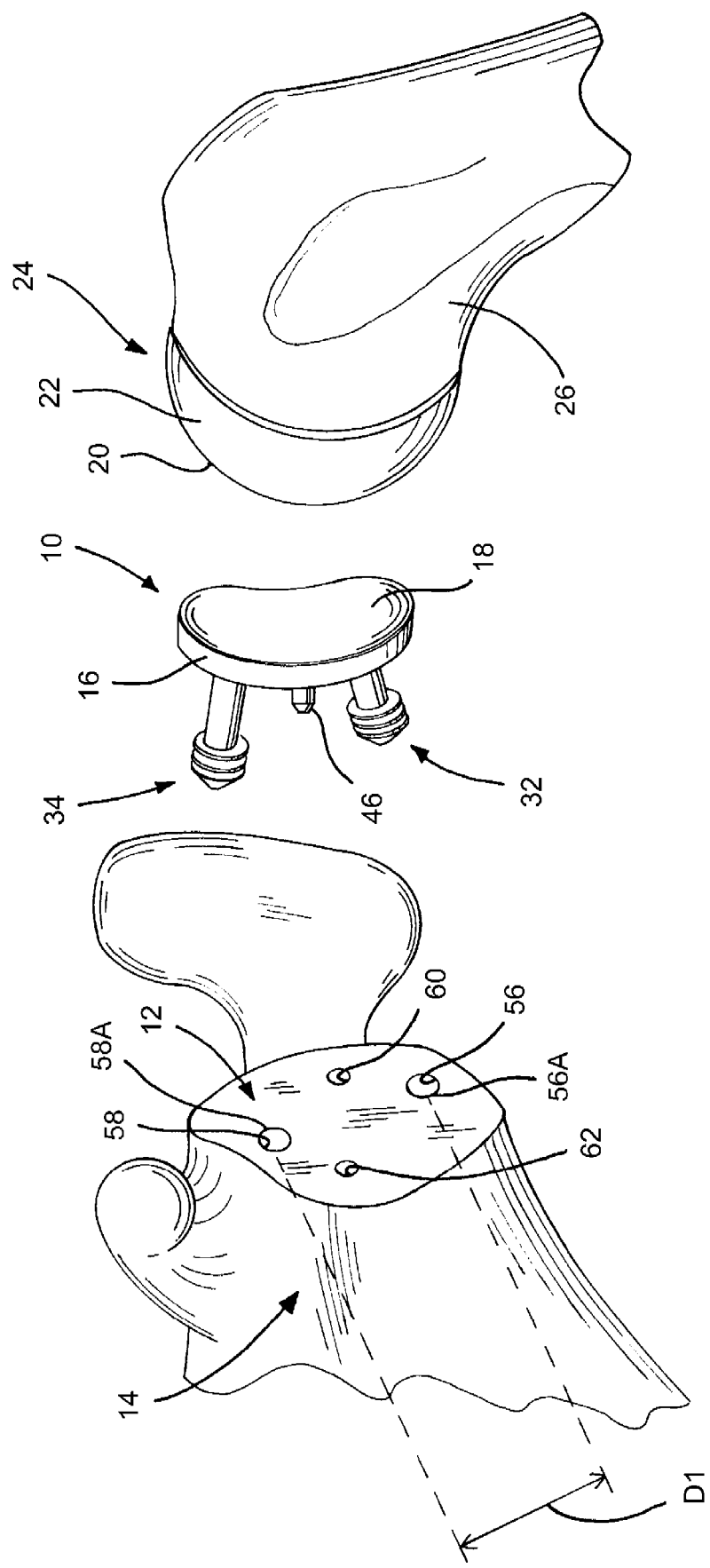
FIG. 1 is an exploded perspective view that shows a glenoid component which incorporates the features of the present disclosure therein positioned between a scapula and a humeral head.

While the glenoid assembly and associated method described herein is susceptible to various modifications and alternative forms, specific embodiments thereof have been shown by way of example in the drawings and will herein be described in detail. It should be understood, however, that there is no intent to limit the glenoid assembly and associated method to the particular forms disclosed, but on the contrary, the intention is to cover all modifications, equivalents, and alternatives falling within the spirit and scope of the invention as defined by the appended claims.

Glenoid Component 10 and Associated Assembly

Referring now to FIG. 1, there is shown a glenoid component 10 that is configured to be implanted in a glenoid region 12 of a scapula 14. The glenoid component 10 includes a base component 16 that defines a bearing surface 18. The bearing surface 18 is configured to mate with a bearing surface 20 of a humeral head 22 of a humeral prosthesis 24. While the humeral head 22 is depicted in FIG. 1 as a prosthetic humeral head secured to a proximal end of a humerus 26, the bearing surface 18 may also mate with a natural head (not shown) of the humerus 26. Also, the humeral prosthesis 24 may be implanted in the humerus 26 using any one of various implantation methods well know to those skilled in the medical arts. As an example, the humeral prosthesis may include a stem (not shown) that is attached to the humeral head 22 and implanted within an intramedullary canal (not shown) of the humerus 26 in a conventional manner.

Figure 2:
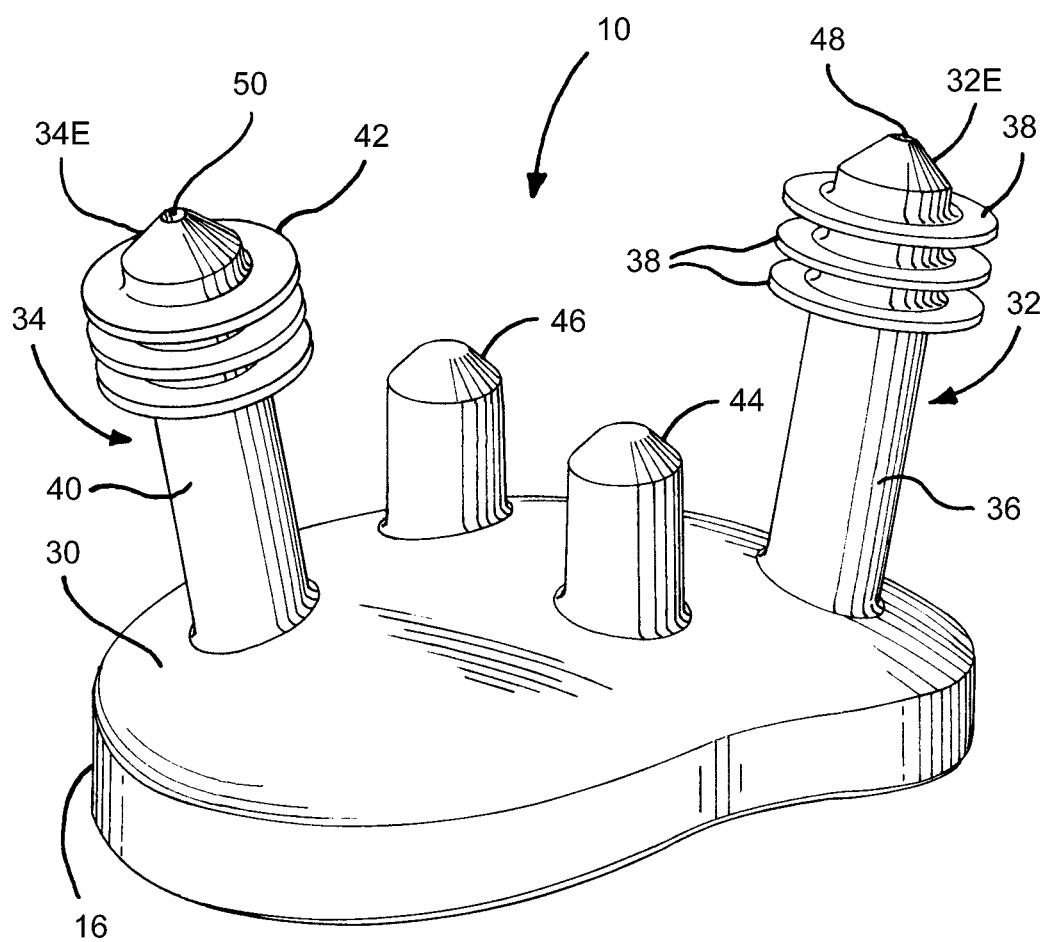
FIG. 2 is a perspective view of the glenoid component of FIG. 1.
Figure 3:
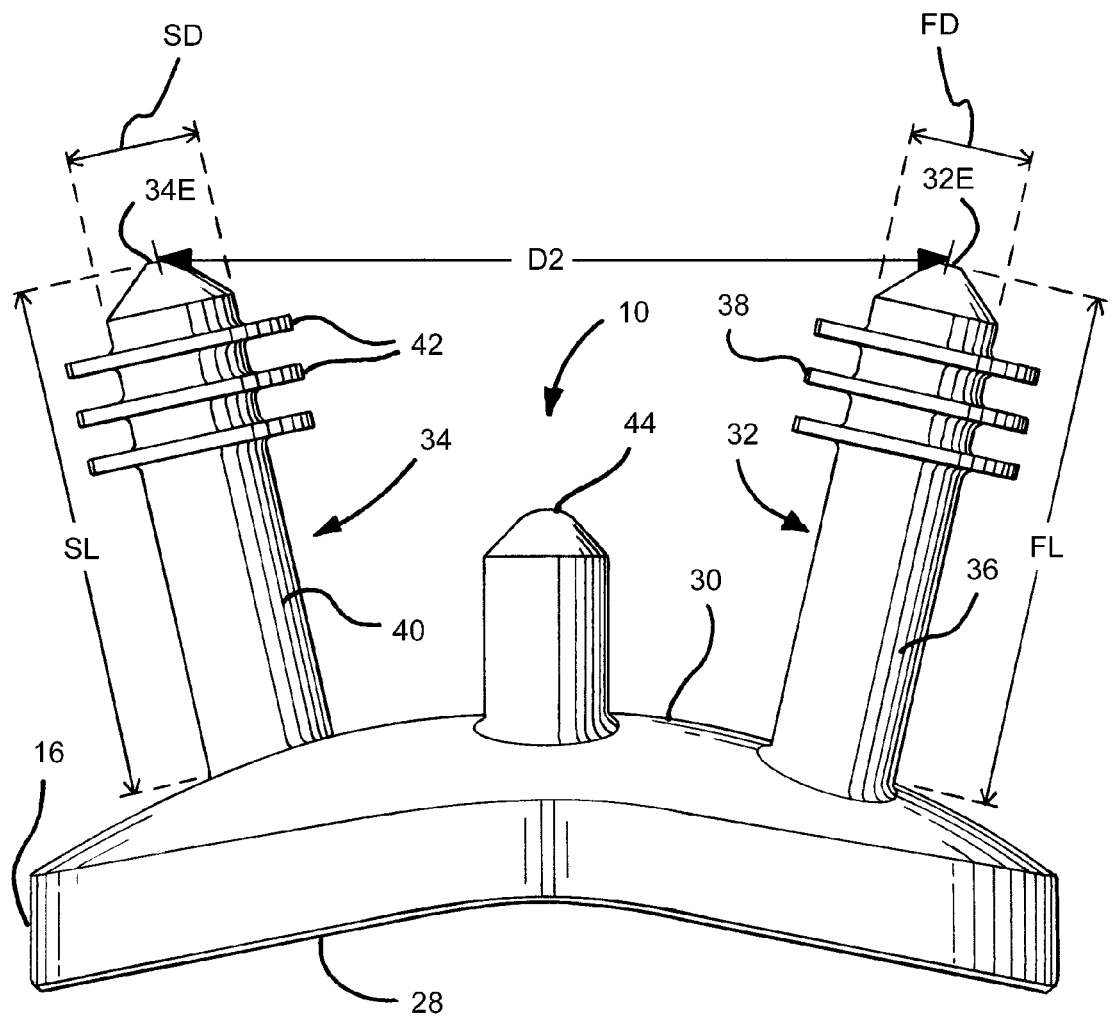
FIG. 3 is a side elevational view of the glenoid component of FIG. 1.
Figure 4:
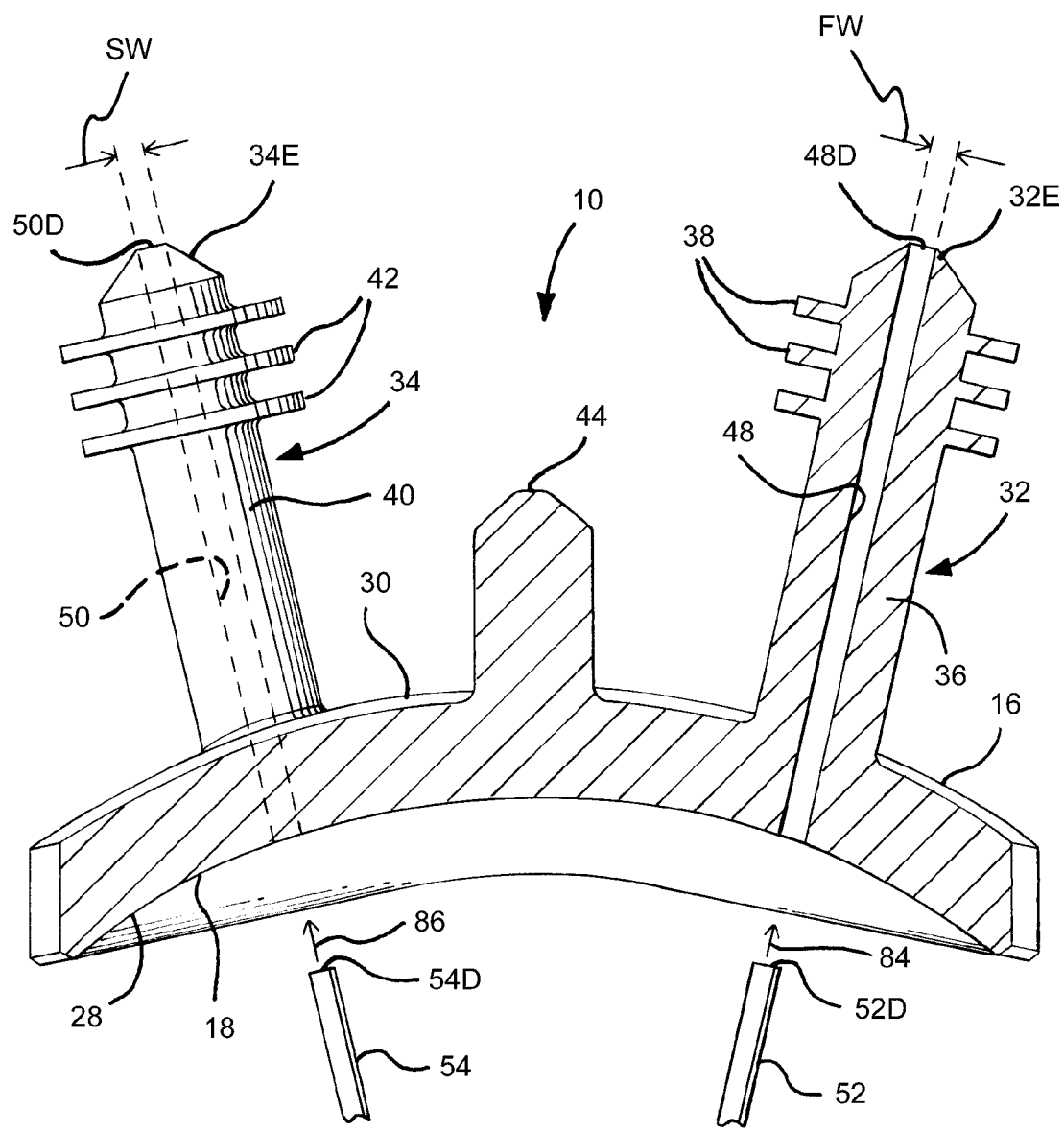
FIG. 4 is a cross sectional view of the glenoid component of FIG. 1, with two stiffening members shown with the glenoid component to form a glenoid assembly.

Turning now to FIGS. 2-4, the glenoid component 10 is shown in more detail. In particular, the base component 16 of the glenoid component 10 has a humeral-facing side 28 and a scapula-facing side 30. The bearing component 18 is defined on the humeral-facing side 28. The glenoid component 10 further includes an anchor peg 32 and another anchor peg 34. The anchor peg 32 has a distal end portion 32E, while the anchor peg 34 has a distal end portion 34E. The anchor pegs 32, 34 extend from the scapula-facing side 30 in non-parallel orientation with respect to each other as shown in FIGS. 2-4. Specifically, the non-parallel orientation is a diverging orientation with respect to each other. The glenoid component 10 additionally includes a stabilizing or anti-rotation peg 44 and another stabilizing or anti-rotation peg 46. The stabilizing pegs 44, 46 extend from the scapula-facing side 30 in parallel orientation with respect to each other as shown in FIGS. 2-4.

In a preferred embodiment, the glenoid component 10 is constructed as a one-piece member of synthetic polymeric material, with the base component 16, the anchor pegs 32, 34, and the stabilizing pegs 44, 46 integrally formed together as shown in FIGS. 2-4. The preferred material used to make the glenoid component 10 is ultra high molecular weight polyethylene, although any known biocompatible material may be used.

The anchor peg 32 includes a shaft 36 and a number of fins 38 extending radially from the shaft 36, while the anchor peg 34 includes a shaft 40 and a number of fins 42 extending radially from the shaft 40. The shaft 36 of the anchor peg 32 defines a first shaft diameter equal to FD and a first shaft length equal to FL, while the shaft 40 of the anchor peg 34 defines a second shaft diameter equal to SD and a second shaft length equal to SL.

Preferably, 15.0 mm<FL<25.0 mm. More preferably, 19.0 mm<FL<21.0 mm. And most preferably FL is equal 19.6 mm. Similarly, preferably, 15.0 mm<SL<25.0 mm. More preferably, 19.0 mm<SL<21.0 mm. And most preferably SL is equal to 19.6 mm.

Preferably, 3.0 mm<FD<4.5 mm. More preferably, 3.3 mm<FD<4.3 mm. And most preferably FD is equal 3.8 mm. Similarly, preferably, 3.0 mm<SD<4.5 mm. More preferably, 3.3 mm<SD<4.3 mm. And most preferably SD is equal 3.8 mm.

The ratio of the first shaft diameter to the first shaft length is FD/FL, while the ratio of the second shaft diameter to the second shaft length is SD/SL. Preferably, 0.14<FD/FL<0.24. More preferably, 0.16<FD/FL<0.22. And most preferably FD/FL is equal to 0.19. Similarly, preferably, 0.14<SD/SL<0.24. More preferably, 0.16<SD/SL<0.22. And most preferably SD/SL is equal to 0.19.

It should be appreciated the values of FD, FL, SD, and SL are selected so that the anchor pegs 32, 34 possess a flexible quality. This is especially true when the glenoid component 10 is made of an ultra high molecular weight polyethylene material.

In order to enhance the flexibility of the anchor pegs 32, 34, the glenoid component is further configured to possess a passageway 48 and another passageway 50. As can be seen in FIGS. 2 and 4, the passageway 48 extends through the shaft 36 of the peg 32, and the passageway 50 extends through the shaft 38 of the peg 34. Both the passageway 48 and the passageway 50 further extend through the base component 16 as shown in FIG. 4. A pair of stiffening members 52, 54 are configured to be respectively received within the passageways 48, 50. The stiffening members 52, 54 are both preferably elongate metal pins having lengths respectively equal to the length of passageways 48, 50. As an example, each pin 52, 54 may be made from stainless steel. The stiffening members 52, 54 are intended to be inserted into the passageways 48, 50 after the glenoid component 10 is implanted into the scapula of a patient as will be discussed in more detail below.

The first passageway 48 has a first width FW, while the second passageway 50 has a second width SW. Preferably, 0.6 mm<FW<0.8 mm. Most preferably, FW is equal to 0.7 mm. Similarly, preferably, 0.6 mm<SW<0.8 mm. Most preferably, SW is equal to 0.7 mm. It should be appreciated that the diameter of the pins 52, 54 are respectively equal to FW, SW (or are slightly less than FW, SW) so that upon insertion of the pins 52, 54, into the passageways 48, 50, respectively, the pins will be retained therein in a friction fit manner. Note that slight elastic deformation of the material defining the sidewalls of the passageways 48, 50 will aid in retaining pins 52, 54 within the passageways 48, 50.

Implantation Method

A method of implanting the glenoid component 10 and associated parts will be described with reference to FIGS. 1 and 5-7. Initially, a bore 56, a bore 58, a bore 60, and a bore 62 are drilled in the scapula 14 in the glenoid region 12 as shown in FIG. 1. The bores 56, 58, 60, and 62 are created to substantially correspond to the angular orientations, lengths, and diameters of the pegs 32, 34, 44, 46 in their relaxed state as shown in FIGS. 1-5. Note that an opening 56A defined by the bore 56 and an opening 58A defined by the bore 58 are offset by a first distance D1 (see FIG. 1). The pegs 32, 34, 44, 46 will be ultimately advanced into the bores later in the procedure. Note that due to the non-parallel orientation the anchor pegs 32, 34, these pegs will have to be flexed prior to insertion of their distal end portions 32E, 34E into the bore openings 56A, 58A. Significantly, in the relaxed state of the pegs 32, 34 of the glenoid component 10, the distal end portion 32E of the peg 32 is offset from the distal end portion 34E of the peg 34 by a distance D2 (see FIG. 3) which is significantly greater than D1. Any attempt to simultaneously advance the end portions 32E, 34E of the pegs respectively into the openings 56A, 58A would be unsuccessful since the offset distance D2 of the end portions 32E, 34E does not correspond to the offset distance D1 of the openings 56A, 58A. What is meant herein by the term "correspond" or "corresponds" with respect to the discussion of distances (e.g. distances D1, D2, and D3 (discussed later)) is that two distances correspond with each other if the two distances are similar enough to enable simultaneous advancement of the distal end portions 32E, 34E into the openings 56A, 58A so that the pegs 32, 34 may be respectively inserted into bores 56, 58. On the other hand, what is meant herein by the phrase "do not correspond" with respect to the discussion of distances (e.g. distances D1, D2, and D3 (discussed later)) is that two distances do not correspond with each other if the two distances are dissimilar enough to prevent simultaneous advancement of the distal end portions 32E, 34E into the openings 56A, 58A so that the pegs 32, 34 cannot be respectively inserted into bores 56, 58.

Figure 6:
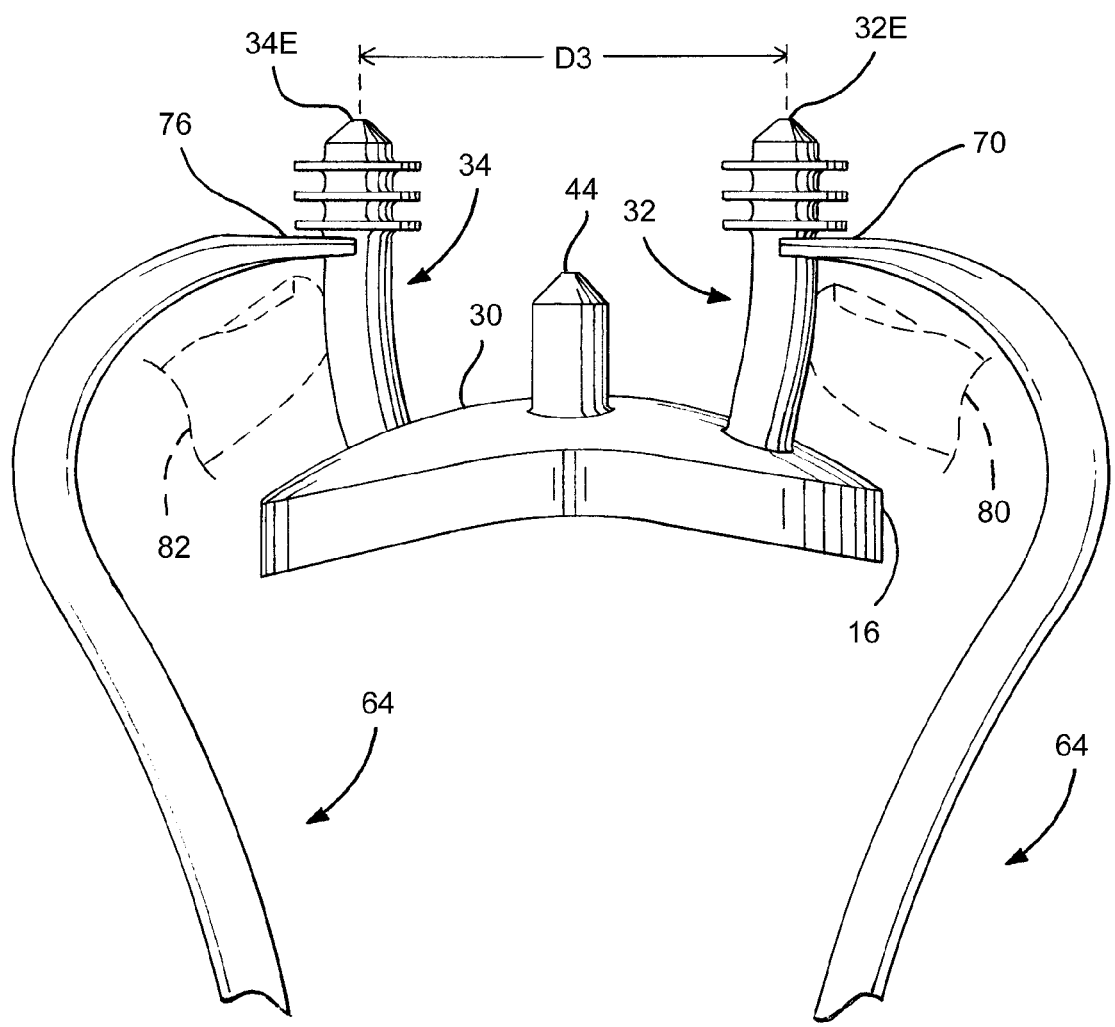
FIG. 6 is a fragmentary side elevational view of the instrument of FIG. 5, and a side elevational view of the glenoid component of FIG. 5, with the anchor pegs of the glenoid component shown in their flexed or bent state.
Figure 7:
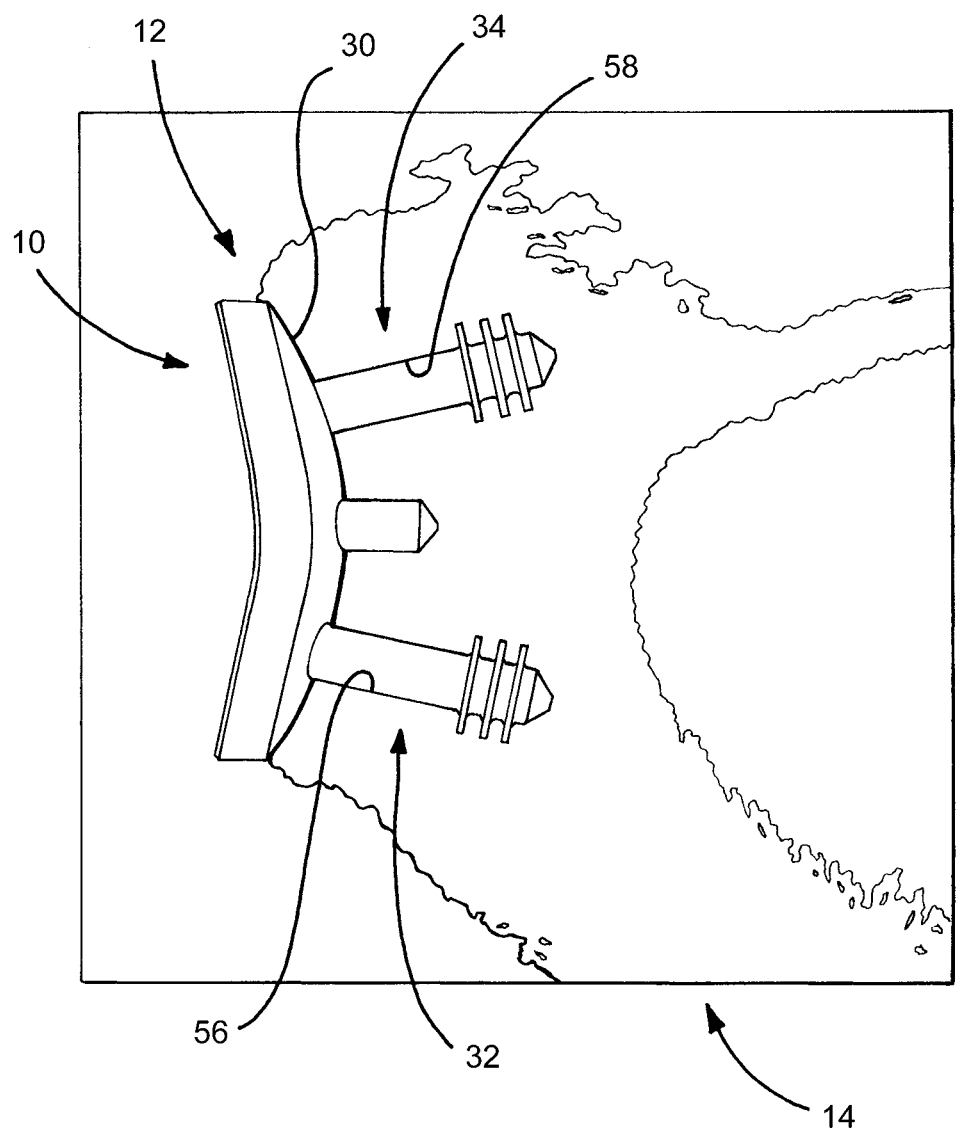
FIG. 7 is a side elevational view of the glenoid assembly of FIG. 4 after it is implanted in the scapula of FIG. 1.

Thus, the next step of the procedure is to flex the peg 32 and the peg 34 so that the first end portion 32E of the first peg 32 and the second end portion 34E of the second peg 34 are offset by a distance D3 (see FIG. 6) which corresponds to the distance D1. The flexing step is performed when the glenoid component 10 is spaced apart from the scapula 14. With the end portions 32E, 34E positioned so that they are offset by the distance D3 as shown in FIG. 6, the end portion 32E of the first peg 32 and the end portion 34E of the second peg 34 are simultaneously advanced through the opening 56A and into the bore 56 and through the opening 58A and into the bore 58A, respectively. Then, the first peg 32 and the second peg 34 are further advanced into the first bore 56 and the second bore 58, respectively, until the scapula-facing side 30 of the base component 16 contacts the scapula 14 in the glenoid region 12 as shown in FIG. 7. Note that upon complete advancement of the pegs 32, 34 into the bores 56, 58, the pegs 32, 34 assume their relaxed state as shown in FIG. 7.

Figure 5:
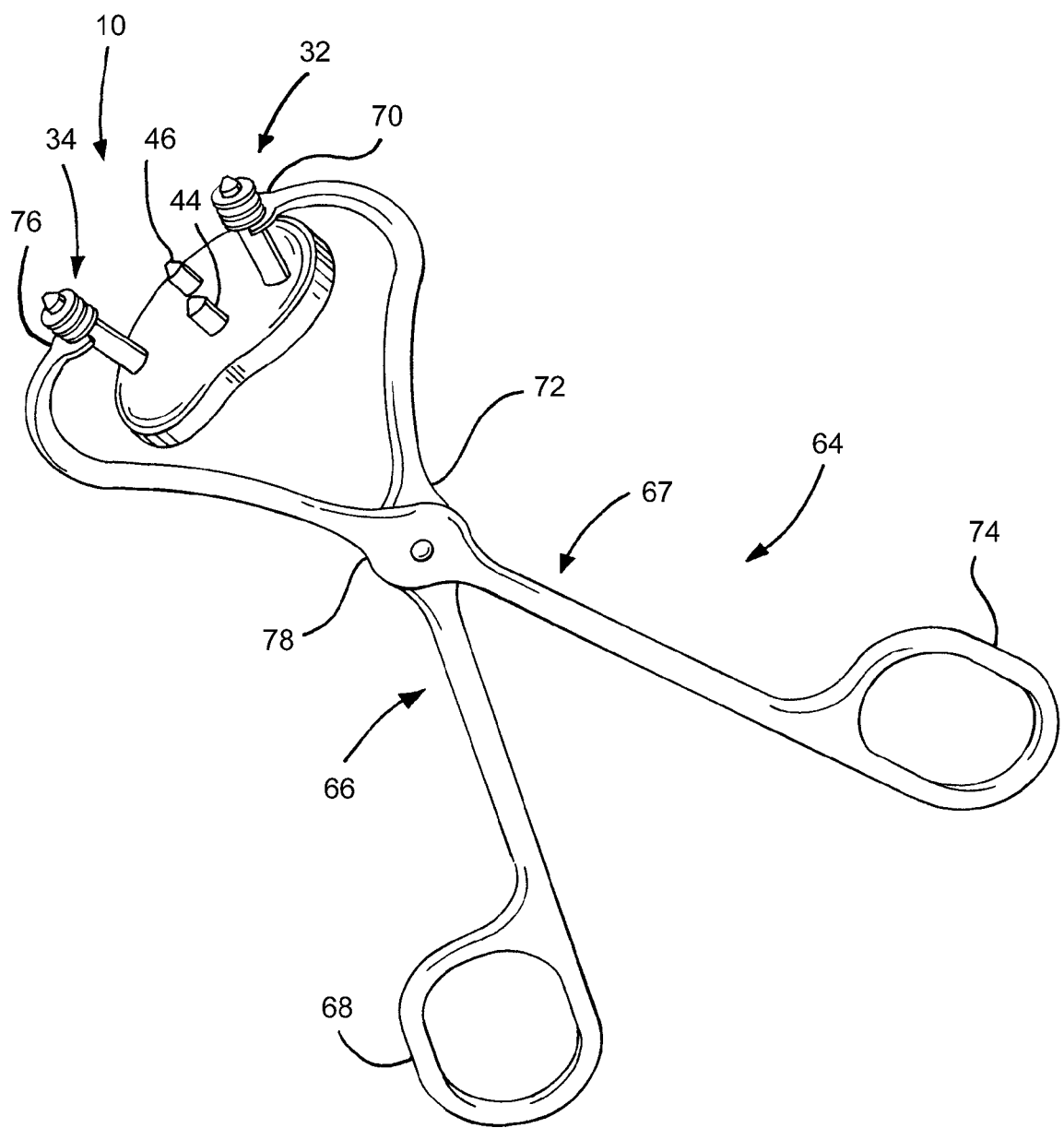
FIG. 5 is a perspective view of an instrument grasping the glenoid component of FIG. 1, with the anchor pegs of the glenoid component shown in their relaxed state.

One preferred manner of performing the flexing step includes the use of an instrument 64 which is shown in FIGS. 5-6. The instrument 64 includes an elongate member 66 and an elongate member 67. The elongate member 66 includes a first handle end portion 68, an opposite first contact end portion 70 configured to contact the peg 32, and a first intermediate portion 72 interposed therebetween. The second elongate member 67 includes a second handle end portion 74, an opposite second contact end portion 76 configured to contact the second peg 34, and a second intermediate portion 78 interposed therebetween. The first intermediate portion 72 is pivotably coupled to the second intermediate portion 78. It should be appreciated that movement of the first handle end portion 68 and the second handle end portion 74 towards each other causes the first contact end portion 70 and the second contact end portion 76 to move towards each other.

Thus, according to this preferred manner of performing the flexing step, the following is performed. Firstly, the first contact end portion 70 is positioned in contact with the first peg 32 and the second contact end portion 76 is positioned in contact with the second peg 34 as shown in FIG. 5. Note that FIG. 5 shows the pegs 32, 34 of the glenoid component 10 in their relaxed state in which the distal end portion 32E of the peg 32 is offset from the distal end portion 34E of the peg 34 by a distance D2 (see also FIG. 3). Then, the first handle end portion 68 and the second handle end portion 74 are moved towards each other by a medical personnel's hand so as to cause the first end portion 32E of the first peg 32 and the second end portion 34E of the second peg 34 to move towards each other until the end portions 32E, 34E are offset by the distance D3 as shown in FIG. 6.

Pursuant to an alternative manner of performing the flexing step, the following is performed. A first finger 80 (shown in phantom in FIG. 6) of a hand of a medical personnel is positioned in contact with the first peg 32 and a second finger 82 (shown in phantom in FIG. 6) of the hand is positioned in contact with the second peg 34. Then, the first finger 80 and the second finger 82 are moved towards each other so as to cause the first end portion 32E of the first peg 32 and the second end portion 34E of the second peg 34 to move towards each other until the end portions 32E, 34E are offset by the distance D3 as shown in FIG. 6.

Next, after full receipt of the pegs 32, 34 within the bores 56, 58 as shown in FIG. 7, the pins 52, 54 are advanced into the passageways 48, 50 in the direction of arrows 84, 86 as shown in FIG. 4. In particular, the pin 52 is advanced within the passageway 48 in the direction of arrow 84 until a distal end 52D of the pin 52 arrives at the distal end 48D of the passageway 48. Similarly, the pin 54 is advanced within the passageway 50 in the direction of arrow 86 until a distal end 54D of the pin 54 arrives at the distal end 50D of the passageway 50. With the pins 52, 54 positioned within the passageways 48, 50, the pegs 52, 54 possess a relatively stiff configuration in comparison to the stiffness of the pegs 52, 54 without the presence of the pins 52, 54 within the passageways 48, 50.

FIG. 7 shows a CT image of the glenoid component 10 after it is implanted in the glenoid region 12 of the scapula 14 in accordance with the above-identified procedure. In particular, the scapula-facing side 30 of the base component 16 is shown contacting the scapula 14. Further, the peg 32 is shown located within the bore 56, while the peg 34 is shown located within the bore 58. In addition, the pin 52 is located within the passageway 48, while the pin 54 is located within the passageway 50. (Note, for clarity of viewing, the pins 52, 54 and passageways 48, 50 are not shown in FIG. 7.)

Glenoid Component 100 and Associated Assembly

Figure 8:
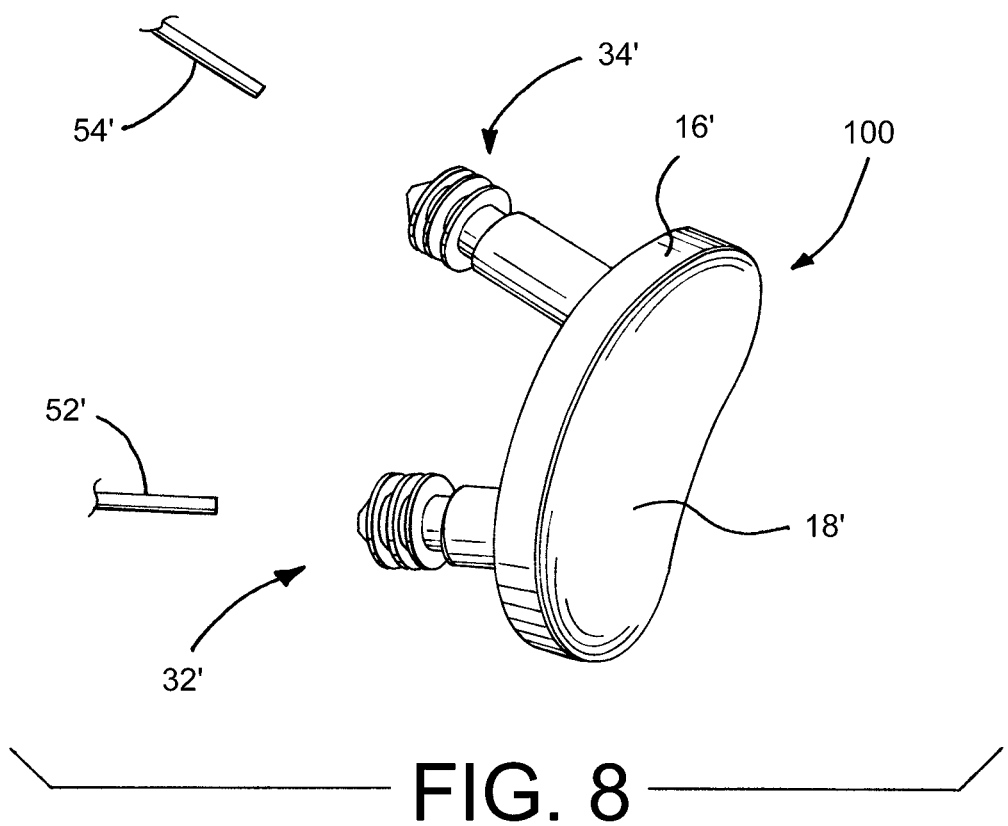
FIG. 8 is a perspective view of an alternative embodiment of a glenoid component and two stiffening members which collectively form an alternative glenoid assembly.
Figure 9:
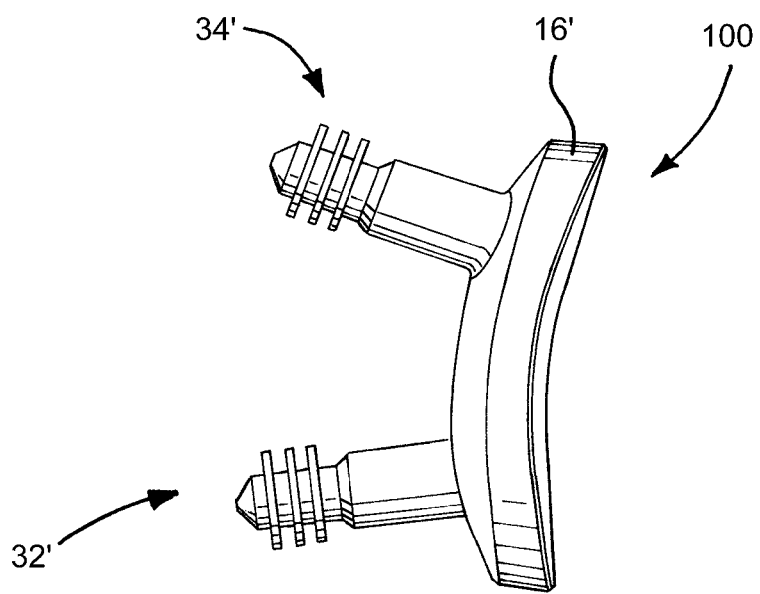
FIG. 9 is a side elevational view of the glenoid component of FIG. 8.

FIGS. 8 and 9 show an alternative embodiment of a glenoid component 100 that is configured, used, and implanted in the exact same manner as the glenoid component 10 of FIGS. 1-7, except for the following distinctions in structure and implantation. The only difference between the structures of the glenoid components 10, 100 is that the glenoid component 100 does not include any stabilizing or anti-rotation pegs (similar to stabilizing pegs 44, 46 of the glenoid component 10). Thus, an associated distinction in the manner of implanting the glenoid component 100 in the glenoid region 12 of the scapula 14 (in comparison to implantation of the glenoid component 10) is that bores 60, 62 (see FIG. 1) do not have to be created in the scapula 14.

Note other parts of the glenoid component 100 are shown in FIGS. 8 and 9. Due to the similarity in configuration of the glenoid component 10 and the glenoid component 100, like numbers are used to describe both glenoid components, with the exception that a single prime symbol is included after each of the various reference numerals indicating various portions of the glenoid component 100 and associated parts. For example, reference numerals 32, 34 are used for indicating the anchor pegs of the glenoid component 10, while the reference numerals 32', 34' are used for indicating the anchor pegs of the glenoid component 100.

As an alternative to the glenoid component 100, instead of configuring the glenoid component to have diverging anchor pegs (e.g. anchor pegs 32', 34'), the alternative glenoid component may have converging anchor pegs (not shown). The angular orientation of such converging anchor pegs may be the mirror image of the divergent anchor pegs 32', 34'. It should be appreciated that an alternative instrument (somewhat like instrument 64") would need to be designed so that movement of the first handle end portion 68' and the second handle end portion 74' towards each other causes the distal end portions of the converging anchor pegs to move away from each other until such end portions are offset by the distance D3 (see, e.g., FIG. 6). Also, the bores 56', 58' would have to be drilled in the scapula to substantially correspond to the angular orientations of the converging pegs in their relaxed state.

Glenoid Component 200 and Associated Assembly

Figure 10:
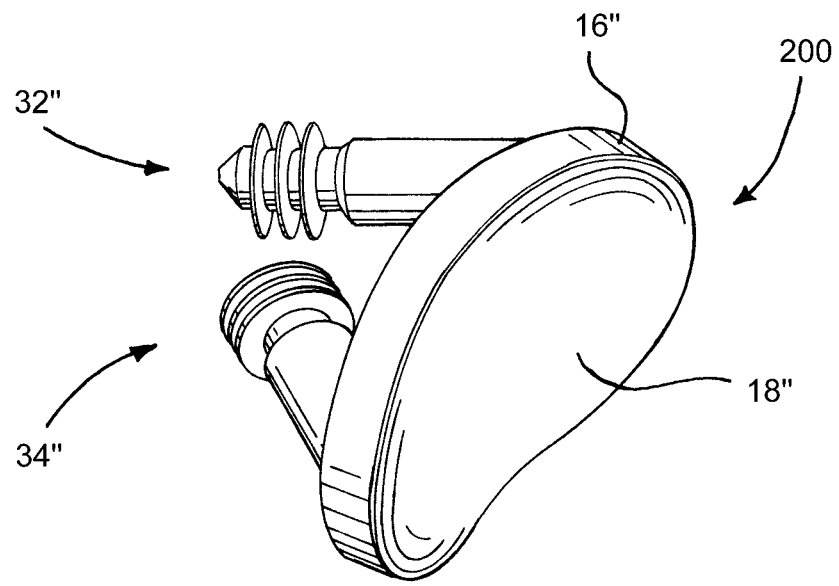
FIG. 10 is a perspective view of yet another alternative embodiment of a glenoid component.
Figure 11:
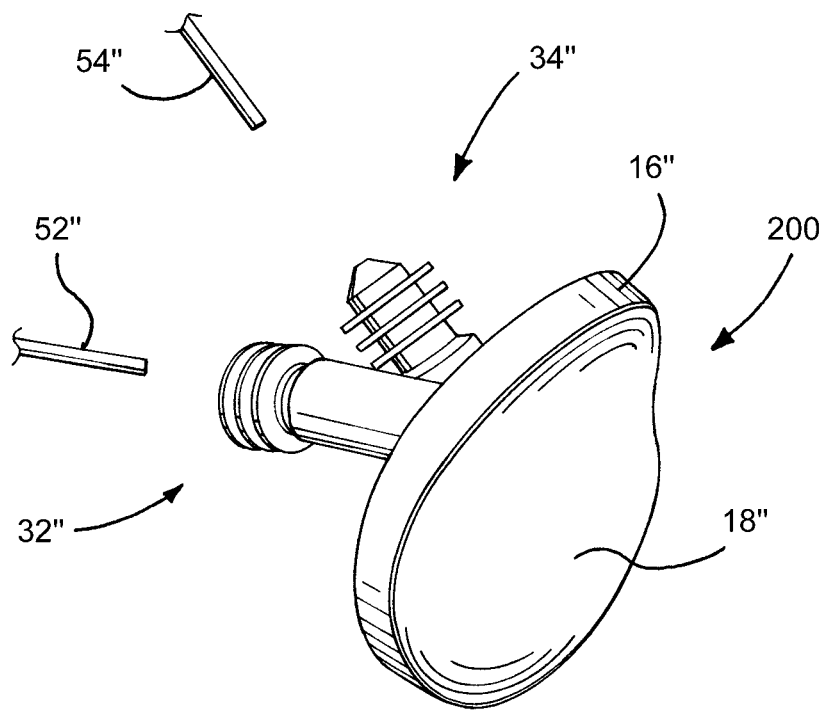
FIG. 11 is another perspective view of the glenoid component of FIG. 11 along with two stiffening members which collectively form another alternative glenoid assembly.

FIGS. 10 and 11 show a further alternative embodiment of a glenoid component 200 that is configured, used, and implanted in the exact same manner as the glenoid component 100 of FIGS. 8-9, except for the following distinction in structure and implantation. The sole difference between the structures of the glenoid components 100, 200 is that the pegs 32", 34" of the glenoid component 200 possess differing angular orientations in comparison to the pegs 32', 34' of the glenoid component 100. The particular angular orientations of the pegs 32", 34" of the glenoid component 200 is shown in FIGS. 10-11. Thus, an associated distinction in the manner of implanting the glenoid component 200 in the glenoid region 12 of the scapula 14 (in comparison to the implantation of the glenoid component 100) is that bores 56, 58 (see FIG. 1) have to be drilled in the scapula to substantially correspond to the angular orientations of the pegs 32", 34" in their relaxed state which is shown in FIGS. 10-11. A further associated distinction in the manner of implanting the glenoid component 200 in the glenoid region 12 of the scapula 14 (in comparison to the implantation of the glenoid component 100) is that the pegs 32", 34" would have to be flexed in different directions so that the first end portion 32E" of the first peg 32" and the second end portion 34E" of the second peg 34" are offset by the distance D3 (see FIG. 6) which corresponds to the distance D1. As with the implantation method described in connection with the glenoid component 10, the pegs 32", 34" could flexed by fingers of a person's hand or an instrument 64". Of course, the instrument 64" would need to be designed so that movement of the first handle end portion 68" and the second handle end portion 74" towards each other by a medical personnel's hand causes the first end portion 32E" of the first peg 32" and the second end portion 34E" of the second peg 34" to move away from each other until the end portions 32E", 34E" are offset by the distance D3 (see, e.g., FIG. 6).

Other parts of the glenoid component 200 are shown in FIGS. 10-11. As was similarly noted with respect to FIGS. 8-9 above, due to the similarity in configuration of the glenoid component 200 and the glenoid component 100, like numbers are used to describe both glenoid components, with the exception that a double prime symbol is included after each of the various reference numerals indicating various portions of the glenoid component 200 and associated parts. For example, reference numerals 32', 34' are used for indicating the anchor pegs of the glenoid component 100, while the reference numerals 32", 34" are used for indicating the anchor pegs of the glenoid component 200.

Glenoid Component 300 and Associated Assembly

Figure 12:
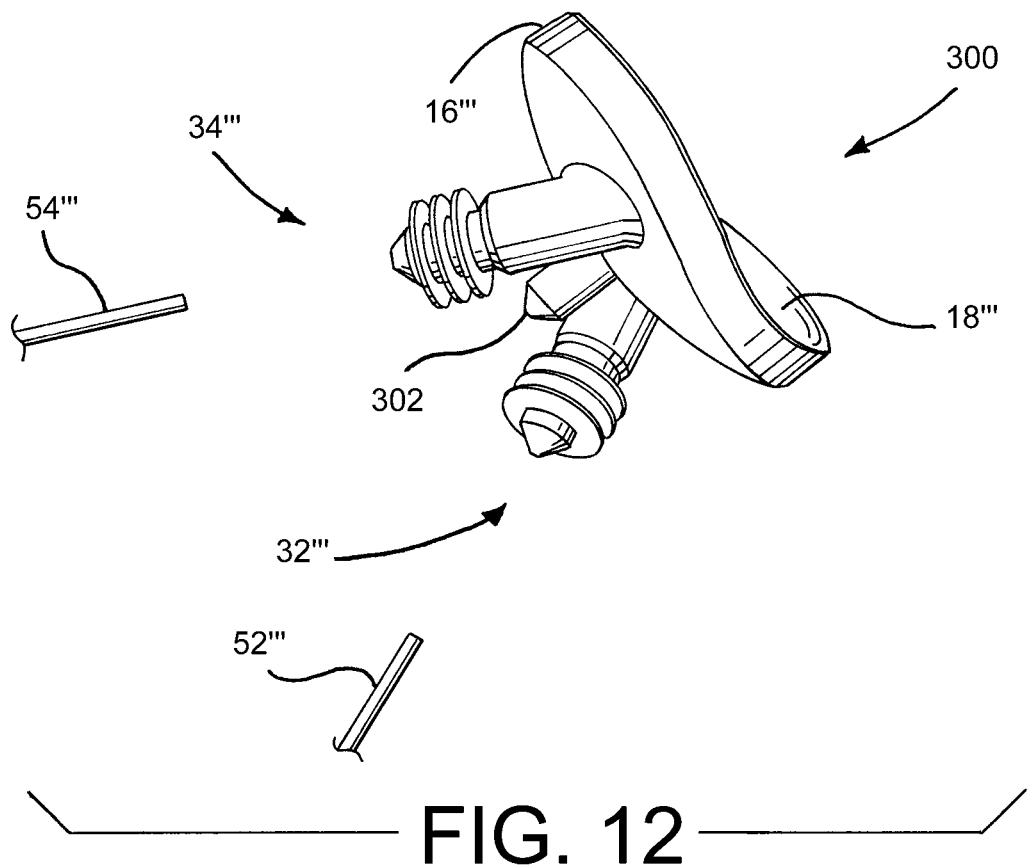
FIG. 12 is a perspective view of still another alternative embodiment of a glenoid component and two stiffening members which collectively form yet still another alternative glenoid assembly.
Figure 13:
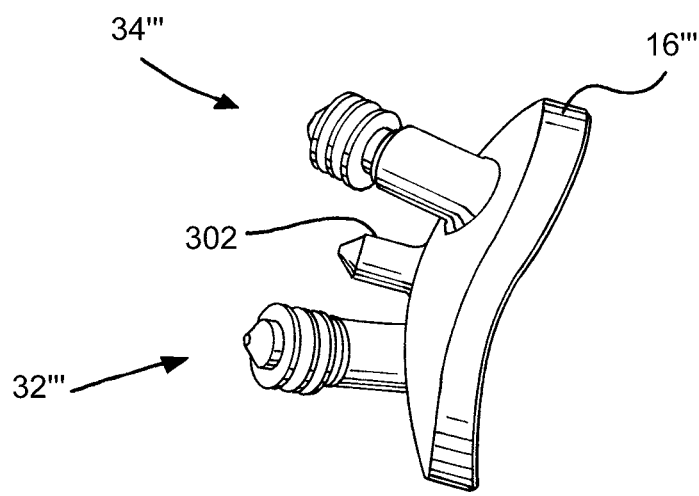
FIG. 13 is a side elevational view of the glenoid component of FIG. 12.

FIGS. 12 and 13 show yet another alternative embodiment of a glenoid component 300 that is configured, used, and implanted in the exact same manner as the glenoid component 200 of FIGS. 10-11, except for the following distinctions in structure and implantation. A first difference between the structures of the glenoid components 200, 300 is that the glenoid component 300 includes a stabilizing peg 302 that is configured exactly as either of the stabilizing pegs 44, 46 of FIGS. 1-7. However, the stabilizing peg 302 extends from the scapula-facing side 30''' of the base component 16''' at a location that is centrally located on the scapula-facing side 30'''. Another difference between the structures of the glenoid components 200, 300 is that the pegs 32''', 34''' of the glenoid component 300 possess differing angular orientations in comparison to the pegs 32", 34" of the glenoid component 200. The particular angular orientations of the pegs 32''', 34''' of the glenoid component 300 is shown in FIGS. 12-13. Thus, an associated distinction in the manner of implanting the glenoid component 300 in the glenoid region 12 of the scapula 14 (in comparison to the implantation of the glenoid component 200) is that the bores 56, 58 (see FIG. 1) have to be drilled in the scapula to substantially correspond to the angular orientations of the pegs 32''', 34''' in their relaxed state which is shown in FIGS. 12-13. Further, a bore (not shown) would have to be drilled in the scapula to substantially correspond to the angular orientation, length, and diameter of the peg 302 which is shown in FIGS. 12-13. A further associated distinction in the manner of implanting the glenoid component 300 in the glenoid region 12 of the scapula 14 (in comparison to the implantation of the glenoid component 200) is that the pegs 32''', 34''' would have to be flexed in different directions so that the first end portion 32E''' of the first peg 32''' and the second end portion 34E''' of the second peg 34''' are offset by the distance D3 (see FIG. 6) which corresponds to the distance D1. As with the implantation method described in connection with the glenoid component 10, the pegs 32''', 34''' could flexed by fingers of a person's hand or an instrument 64'''. Of course, the instrument 64''' would need to be redesigned so that movement of the first handle end portion 68''' and the second handle end portion 74''' towards each other by a medical personnel's hand causes the first end portion 32E''' of the first peg 32''' and the second end portion 34E''' of the second peg 34''' to move with respect to each other until the end portions 32E''', 34E''' are offset by the distance D3 (see, e.g., FIG. 6).

As with the alternative glenoid components 100, 200, other parts of the glenoid component 300 are shown in FIGS. 12-13. As was similarly noted with respect to FIGS. 10-11 above, due to the similarity in configuration of the glenoid component 300 and the glenoid component 200, like numbers are used to describe both glenoid components, with the exception that a triple prime symbol is included after each of the various reference numerals indicating various portions of the glenoid component 300 and associated parts. For example, reference numerals 32", 34" are used for indicating the anchor pegs of the glenoid component 200, while the reference numerals 32''', 34''' are used for indicating the anchor pegs of the glenoid component 300.

Instrument 400

Figure 14:
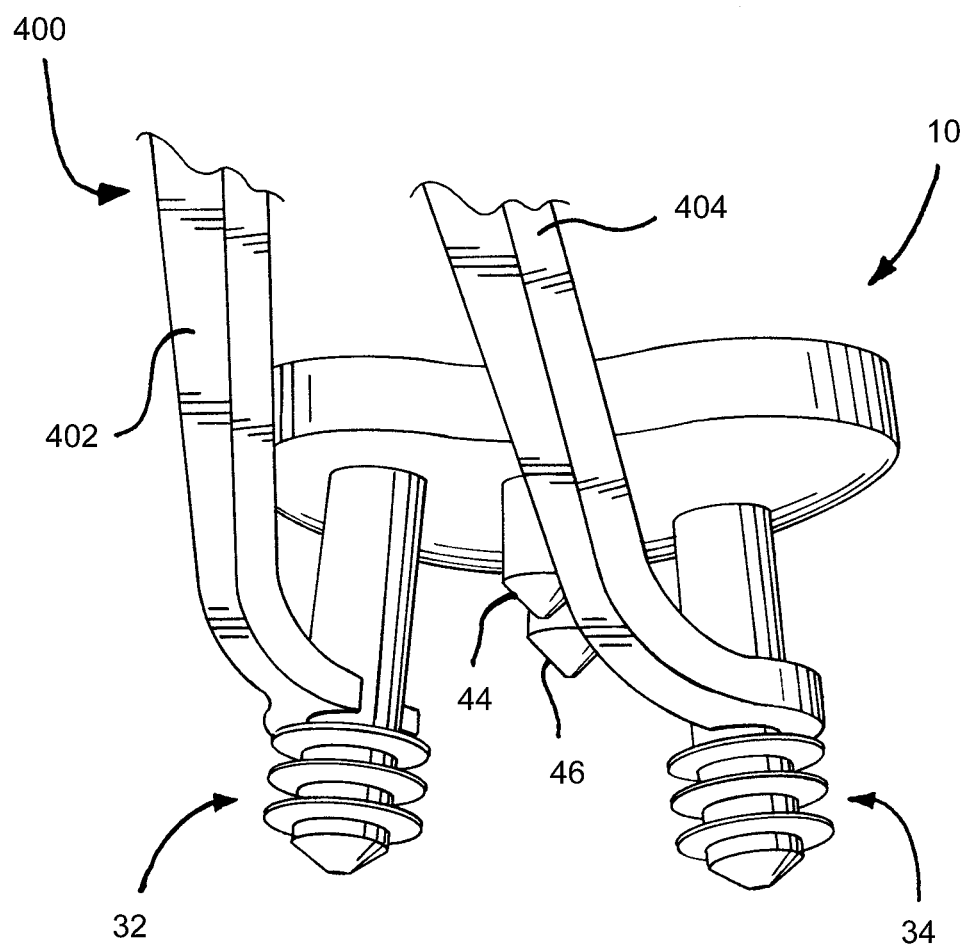
FIG. 14 is a fragmentary perspective view of an alternative instrument for grasping the glenoid component of FIG. 1, with the instrument approaching the anchor pegs from a common side.
Figure 15:
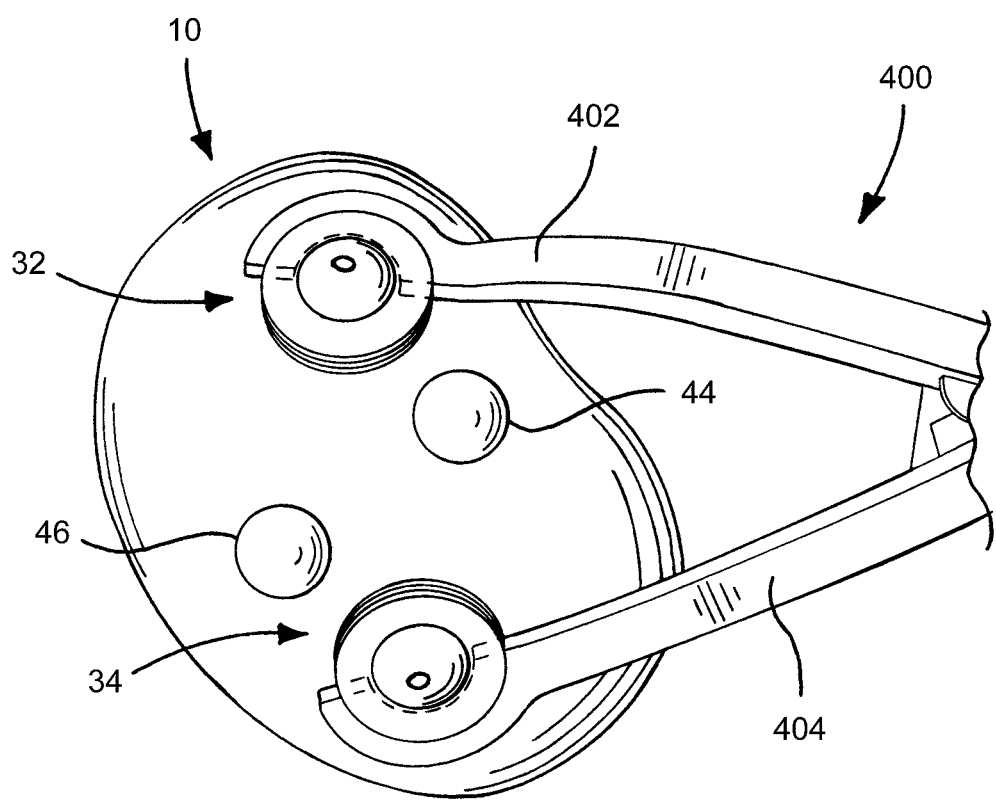
FIG. 15 is another fragmentary perspective view of the instrument for grasping the glenoid component of FIG. 14, but showing the instrument approaching the anchor pegs from a slightly different angle in comparison to the approach shown in FIG. 14.

FIGS. 14 and 15 show an alternative embodiment of an instrument 400 that is used in place of the instrument 64 (see FIGS. 5-6) to perform the flexing step discussed above. The instrument 400 is similar in construction and operation to the instrument 64 in the sense that it is a generally scissors-shaped device. Also, the instrument 400 is used in the exact same manner as the instrument 64 as discussed above to carry out the implantation of the glenoid component 10, with one exception. In particular, as shown in FIG. 14, the two distal arm segments (i.e. distal arm segments 402 and 404) approach the anchor pegs 32, 34 from a common side of the glenoid component 10 during an implantation procedure instead of approaching from opposite sides (as shown in FIGS. 5-6 in connection with the use of instrument 64). FIG. 15 also shows the instrument 400 approaching the anchor pegs 32, 34 from a common side similar to FIG. 14, but from a slightly different direction. It should be appreciated that many manners of approaching the anchor pegs 32, 34 with an instrument (e.g. instrument 64, 400) are possible during implantation of the glenoid component 10.

There is a plurality of advantages arising from the various features of each of the embodiments of the glenoid assembly and associated method described herein. It will be noted that alternative embodiments of the glenoid assembly and associated method may not include all of the features described yet still benefit from at least some of the advantages of such features. Those of ordinary skill in the art may readily devise their own implementations of the glenoid assembly and associated method that incorporate one or more of the features and fall within the spirit and scope of the present invention as defined by the appended claims.

What is claimed is:

1. A method of implanting a glenoid component that includes (i) a base component having a bearing surface defined on a humeral-facing side thereof, (ii) a first peg extending from a scapula-facing side of the base component, (iii) a second peg extending from the scapula-facing side of the base component, the first peg and the second peg being positioned in non-parallel orientation with respect to each other, and (iv) a first and a second stabilizing peg extending from the scapula-facing side of the base component, the first and second stabilization pegs each having a length that is less than a length of the first and the second anchor pegs, the method comprising:

creating a first bore and a second bore in a glenoid region of a scapula for the first peg and the second peg, respectively, so that a first opening defined by the first bore and a second opening defined by the second bore are offset by a first distance, and creating a third bore and a fourth bore in the glenoid region for the first and the second stabilization pegs;

flexing at least one of the first peg and the second peg so that a first end portion of the first peg and a second end portion of the second peg are offset by a second distance which corresponds to the first distance;

advancing the first end portion of the first peg and the second end portion of the second peg into the first bore and the second bore, respectively, while the first end portion of the first peg and the second end portion of the second peg are offset by the second distance; and advancing the first stabilization peg and the second stabilization peg into the third bore and the fourth bore, respectively, after advancing the first end portion of the first peg and the second end portion of the second peg into the first and second bore, respectively, wherein the glenoid component further defines a first passageway and a second passageway, the first passageway extending through the first shaft of the first peg, and the second passageway extending through the second shaft of the second peg.

2. The implantation method of claim 1, further comprising:

further advancing the first peg and the second peg into the first bore and the second bore, respectively, until the scapula-facing side of the base component contacts the scapula;

advancing the first stabilization peg and the second stabilization peg into the third bore and the fourth bore, respectively, after advancing the first end portion of the first peg and the second end portion of the second peg into the first and second bore, respectively, and before the scapula-facing side of the base component contacts the scapula.

3. The implantation method of claim 1, wherein the flexing step includes the step of bending the first peg and the second peg with an instrument while the first peg and the second peg are spaced apart from the scapula.

4. The implantation method of claim 3, wherein:

the instrument includes (i) a first elongate member having a first handle end portion, an opposite first contact end portion configured to contact the first peg, and a first intermediate portion interposed therebetween, and (ii) a second elongate member having a second handle end portion, an opposite second contact end portion configured to contact the second peg, and a second intermediate portion interposed therebetween, the first intermediate portion is pivotably coupled to the second intermediate portion, movement of the first handle end portion and the second handle end portion towards each other causes the first contact end portion and the second contact end portion to move towards each other, and the flexing step includes the steps of (i) positioning the first contact end portion in contact with the first peg and the second contact end portion in contact with the second peg, and (ii) moving the first handle end portion and the second handle end portion towards each other during step (i) so as to cause the first end portion of the first peg and the second end portion of the second peg to be offset by the second distance.

5. The implantation method of claim 1, wherein:

the first peg and the second peg are positioned in a divergent orientation with respect to each other, and the flexing step includes the step of bending the first peg and the second peg towards each until the first end portion of the first peg and the second end portion of the second peg become offset by the second distance.

6. The implantation method of claim 1, wherein:

the first peg includes a first shaft and a first plurality of fins extending radially from the first shaft, and the second peg includes a second shaft and a second plurality of fins extending radially from the second shaft.

7. The implantation method of claim 6, wherein:

the first shaft defines a first shaft diameter equal to FD and a first shaft length equal to FL, the second shaft defines a second shaft diameter equal to SD and a second shaft length equal to SL, $0.14 < FD/FL < 0.24$, and $0.14 < SD/SL < 0.24$.

8. The implantation method of claim 7, wherein:

15.0 mm $<$ FL $<$ 25.0 mm, and 15.0 mm $<$ SL $<$ 25.0 mm.

9. The implantation method of claim 7, wherein:

19.0 mm $<$ FL $<$ 21.0 mm, 19.0 mm $<$ SL $<$ 21.0 mm, $0.16 < FD/FL < 0.22$, and $0.16 < SD/SL < 0.22$.

10. The implantation method of claim 9, wherein:

the first passageway has a first width FW, the second passageway has a second width SW, 0.6 mm $<$ FW $<$ 0.8 mm, and 0.6 mm $<$ SW $<$ 0.8 mm.

11. The implantation method of claim 1, wherein the flexing step includes the step of bending both the first peg and the second peg until the first end portion of the first peg and the second end portion of the second peg become offset by the second distance.

* * * * *